US009642642B2

(12) United States Patent
Lim (10) Patent No.: US 9,642,642 B2
(45) Date of Patent: May 9, 2017

(54) GUIDE TIP INTRODUCER AND METHOD TO CREATE THEREOF

(71) Applicant: Kok Hoo Lim, Beavercreek, OH (US)

(72) Inventor: Kok Hoo Lim, Beavercreek, OH (US)

( * ) Notice: Subject to any disclaimer, the term of this patent is extended or adjusted under 35 U.S.C. 154(b) by 428 days.

(21) Appl. No.: 14/281,256

(22) Filed: May 19, 2014

(65) Prior Publication Data

US 2015/0083776 A1    Mar. 26, 2015

Related U.S. Application Data

(60) Provisional application No. 61/880,239, filed on Sep. 20, 2013.

(51) Int. Cl.
*A61B 17/32* (2006.01)
*A61B 17/072* (2006.01)
*A61M 25/00* (2006.01)
*A61B 17/00* (2006.01)

(52) U.S. Cl.
CPC ........ *A61B 17/32* (2013.01); *A61B 17/07207* (2013.01); *A61M 25/00* (2013.01); *A61B 2017/00473* (2013.01); *A61B 2017/00526* (2013.01); *A61B 2017/320052* (2013.01); *A61B 2017/320056* (2013.01); *Y10T 29/49716* (2015.01)

(58) Field of Classification Search
CPC .......... A61B 19/34; A61B 2018/00916; A61B 17/122; A61B 17/10; A61B 17/02; A61B 17/064; A61B 17/083; A61B 17/1227; A61L 2202/24

USPC ............ 227/175.1–182.1; 606/139, 142, 143
See application file for complete search history.

(56) References Cited

U.S. PATENT DOCUMENTS

| | | | | |
|---|---|---|---|---|
| 2,007,626 A | * | 7/1935 | Waring | A61M 31/00 604/218 |
| 2,887,111 A | * | 5/1959 | Leyro Diaz | A61B 17/282 606/148 |
| 4,505,414 A | * | 3/1985 | Filipi | A61B 17/115 227/155 |
| 5,014,899 A | * | 5/1991 | Presty | A61B 17/07207 227/151 |
| 5,069,097 A | * | 12/1991 | Mori | B26D 1/185 83/455 |
| 5,322,055 A | * | 6/1994 | Davison | A61B 17/320068 601/2 |
| 5,330,486 A | * | 7/1994 | Wilk | A61B 17/068 227/179.1 |
| 5,389,067 A | * | 2/1995 | Rejai | A61F 13/26 493/269 |

(Continued)

*Primary Examiner* — Robert Long (57) ABSTRACT

A guide tip introducer is provided as a compatible attachment for a wide range endoscopic staplers of different makes and models. The guide tip introducer mounts to the anvil of an existing endoscopic stapler in order to facilitate the positioning of the stapler beneath a target structure, reducing the amount tissue needing to be dissected. The guide tip introducer is easy to attach and remove from the anvil tip through its particular shape and through the use of a magnetic attachment strip. The guide tip introducer is constructed from smooth semi-rigid material enabling guidance of the endoscopic stapler while minimizing damage around target structures. The guide tip introducer is fashioned using commonly available material found in most standard operating rooms.

6 Claims, 10 Drawing Sheets

(56) References Cited

U.S. PATENT DOCUMENTS

| | | | | |
|---|---|---|---|---|
| 5,395,033 A * | 3/1995 | Byrne | A61B 17/07207 | 227/175.1 |
| 5,397,324 A * | 3/1995 | Carroll | A61B 17/07207 | 128/898 |
| 5,403,326 A * | 4/1995 | Harrison | A61B 17/0643 | 128/898 |
| 5,404,870 A * | 4/1995 | Brinkerhoff | A61B 17/00 | 227/175.1 |
| 5,665,100 A * | 9/1997 | Yoon | A61B 17/12013 | 606/139 |
| 5,766,187 A * | 6/1998 | Sugarbaker | A61B 17/00 | 606/139 |
| 5,814,057 A * | 9/1998 | Oi | A61B 17/072 | 227/178.1 |
| 5,893,855 A * | 4/1999 | Jacobs | A61B 17/0684 | 606/150 |
| 5,957,430 A * | 9/1999 | Olson | B25C 11/02 | 254/28 |
| 6,206,823 B1 * | 3/2001 | Kolata | A61B 17/00008 | 600/127 |
| 7,182,239 B1 * | 2/2007 | Myers | A61B 17/115 | 227/175.1 |
| 7,434,717 B2 * | 10/2008 | Shelton, IV | A61B 17/105 | 227/175.1 |
| 7,451,765 B2 * | 11/2008 | Adler | A61B 17/12104 | 128/200.26 |
| 7,621,925 B2 * | 11/2009 | Saadat | A61B 17/0401 | 606/139 |
| 7,874,981 B2 * | 1/2011 | Whitman | A61B 17/3421 | 600/184 |
| 7,901,416 B2 * | 3/2011 | Nolan | A61B 17/1114 | 227/175.1 |
| 7,914,543 B2 * | 3/2011 | Roth | A61B 17/07207 | 227/175.1 |
| 7,928,281 B2 * | 4/2011 | Augustine | A61F 13/0203 | 602/42 |
| 8,662,370 B2 * | 3/2014 | Takei | A61B 17/115 | 227/179.1 |
| 8,801,743 B2 * | 8/2014 | Giotis | A61B 17/32053 | 606/187 |
| 2002/0099370 A1 * | 7/2002 | Schulze | A61B 18/1445 | 606/50 |
| 2002/0099372 A1 * | 7/2002 | Schulze | A61B 17/00008 | 606/51 |
| 2002/0099375 A1 * | 7/2002 | Hess | A61B 18/1445 | 606/51 |
| 2002/0117534 A1 * | 8/2002 | Green | A61B 17/0684 | 227/176.1 |
| 2003/0028178 A1 * | 2/2003 | Chin | A61B 46/10 | 606/1 |
| 2004/0243151 A1 * | 12/2004 | Demmy | A61B 17/068 | 606/139 |
| 2005/0236459 A1 * | 10/2005 | Gresham | A61B 17/068 | 227/175.1 |
| 2006/0020213 A1 * | 1/2006 | Whitman | A61B 1/05 | 600/478 |
| 2007/0051375 A1 * | 3/2007 | Milliman | A61B 17/3423 | 128/856 |
| 2007/0282356 A1 * | 12/2007 | Sonnenschein | A61B 17/068 | 606/153 |
| 2009/0114233 A1 * | 5/2009 | Edoga | A61B 17/068 | 128/898 |
| 2009/0163937 A1 * | 6/2009 | Kassab | A61B 17/122 | 606/151 |
| 2009/0204108 A1 * | 8/2009 | Steffen | A61B 17/068 | 606/1 |
| 2010/0084451 A1 * | 4/2010 | Abla | B25C 1/00 | 227/107 |
| 2010/0094315 A1 * | 4/2010 | Beardsley | A61B 17/07207 | 606/143 |
| 2010/0147922 A1 * | 6/2010 | Olson | A61B 17/072 | 227/176.1 |
| 2010/0163598 A1 * | 7/2010 | Belzer | A61B 17/115 | 227/181.1 |
| 2011/0022032 A1 * | 1/2011 | Zemlok | A61B 17/07207 | 606/1 |
| 2011/0087279 A1 * | 4/2011 | Shah | A61B 17/07207 | 606/219 |
| 2011/0114697 A1 * | 5/2011 | Baxter, III | A61B 17/115 | 227/175.1 |
| 2012/0209303 A1 * | 8/2012 | Frankhouser | A61B 10/025 | 606/169 |
| 2013/0075446 A1 * | 3/2013 | Wang | A61B 17/068 | 227/176.1 |
| 2013/0153630 A1 * | 6/2013 | Miller | A61B 17/1155 | 227/175.2 |
| 2013/0256383 A1 * | 10/2013 | Aronhalt | A61B 17/068 | 227/180.1 |
| 2014/0158741 A1 * | 6/2014 | Woodard, Jr. | A61B 17/0401 | 227/175.1 |
| 2014/0166727 A1 * | 6/2014 | Swayze | A61B 17/1155 | 227/179.1 |
| 2014/0319197 A1 * | 10/2014 | Demmy | A61B 17/068 | 227/175.1 |

\* cited by examiner

GUIDE TIP INTRODUCER AND METHOD TO CREATE THEREOF

The current application claims a priority to the U.S. Provisional Patent application Ser. No. 61/880,239 filed on Sep. 20, 2013.

FIELD OF THE INVENTION

The present invention relates generally to surgical instruments, more specifically to a particular attachment for an endoscopic stapler that facilitates

BACKGROUND OF THE INVENTION

One universal truth is that human beings are fairly fragile life forms. For thousands of years, humans have been vulnerable to receiving physical injuries, and are very susceptible to various different diseases, genetic defects, and pathogen infections. In general, people do not like to see other people suffering, and physical injuries and diseases are one of the most prominent forms of suffering as has been shown time and time again throughout human history. In direct response to this fact, compassionate people around the world have worked to better our understanding of the human body with the intention of learning new ways to help those who are suffering from injuries or disease. The study of the human body and the injuries and diseases which afflict it is known as the field of medicine. The field of medicine has been around for many centuries, and humanity has made significant gains in general knowledge, methodology, and treatments within the medical field. There are an incredible number of diseases and injuries which can be cured or repaired in the modern world which was simply beyond our understanding in the past. A person who dedicates their lives to the study and practice of medicine is typically called a physician. In the past, nearly all medical practitioners were known as physicians, however in the modern world there are many different career paths within the field of medicine. Only those who have graduated from medical school with a Doctor of Medicine degree are technically physicians, although they are more commonly called Doctors in the world today.

Some historical physicians who laid the basis for a logical and philosophical approach to medicine include the ancient Egyptian Imhotep, and the ancient Greek physician Hippocrates. A logical approach to medicine based upon observable facts is in contrast with a mystical approach to medicine as was held for many generations in cultures throughout the world. Although the work of Imhotep and Hippocrates were based upon often incorrect anatomy, it was such people willing to search for natural causes of diseases and symptoms who laid the basis for the advancement of the field of medicine to the heights it has achieved in the modern world. Over the years humanity has broadened, improved, and refined its understanding of the physical human body. This increase in understanding has allowed for identification and treatment of diseases and physical injuries which were beyond comprehension and repair in the past.

There are a great many methods and technologies which are associated with the field of medicine and all of them have some specific purpose. Relating to the specific area of surgery, there is an incredible number of new technologies which have been developed to make surgery more efficient, more effective, and less intrusive for the patient. One of the more recent and radical advancements in the surgery is the rapidly developing field or robotic surgery; also known as computer-assisted surgery, and robotically-assisted surgery. Robotic surgery was developed to both increases the effectiveness of open surgery, and to overcome many of the limitations involved with minimally invasive surgery. Minimally invasive surgery involves making the smallest incision possible that is necessary to carry out the surgical procedure. In the past, minimally invasive surgery was very limited as it was very difficult for the surgeon to see what they were doing, oftentimes relying on ultrasound or endoscopic cameras. Robotic surgery has a great advantage in that only a small incision is needed to allow the robotic arms into the body cavity where surgery is being performed. Additionally, the robotic arms possess a plurality of incredibly precise servo motors which allow the arm to actuate about many different axes, thus enabling the surgeon to maneuver around organs and arteries with great efficiency. Additionally, most robotic surgery machines incorporate at least one camera arm to allow for clear viewing of the procedure being carried out; in robotic surgery, the machine is typically controlled by a trained physician.

Despite the advantages of robotic surgery as described above, the procedure does still have some limitations. One such limitation is the need for a bedside surgeon who may be another physician, a physician's assistant, or a certified nurse practitioner. This bedside surgeon is typically responsible for operation an endoscopic stapler which is used to rejoin severed tissues such that they will fuse back together properly when healing. The endoscopic stapler comprises a thin stem which is inserted into the body cavity where the surgery is being performed. The anvil of the stapler is typically guided beneath the structure to be stapled, and then the stapler is activated. Unfortunately it can be quite difficult to maneuver the stapler into place; a task that is made difficult by the fact that the person maneuvering the stapler only has a two dimensional view of the body cavity. It is imperative that the person operating the stapler does not graze any arteries or veins, as they could be damaged which subsequently results in life threatening internal bleeding. Most available endoscopic staplers have a fairly blunt and wide anvil, thereby making it very difficult to maneuver the anvil past arteries and underneath structures. Some endoscopic staplers make use of a guiding tip, however these tips are often specialized to one make or model of endoscopic stapler. There is a need for a guide tip which can be applied to virtually any make or model of endoscopic stapler, thereby ensuring that the surgeon is able to be maximally efficient with the tools that are available to them.

It is an object of the present invention to introduce a guide tip for endoscopic stapler which is compatible with a broad range of different makes and models of endoscopic staplers. It is a further object of the present invention that the guide tip be easy to place on the anvil, and easy to remove from the anvil. It is a further object of the present invention to comprise some smooth semi-rigid material which enables guidance of the endoscopic stapler while minimizing the chances that an artery or vein will be damaged by contact with the guide tip. It is a further object of the present invention to make use of magnetic attraction in order to secure the guide tip to the anvil in a way that is both effective and easy to use.

DETAIL DESCRIPTIONS OF THE INVENTION

All illustrations of the drawings are for the purpose of describing selected versions of the present invention and are not intended to limit the scope of the present invention.

Referencing FIG. 1 and FIG. 5-7, the present invention is a guide tip introducer 100 that mounts to the anvil of an existing endoscopic stapler 200 in order to facilitate the positioning of the stapler beneath a target structure, reducing the amount tissue needing to be dissected. In the current embodiment of the present invention, the guide tip introducer 100 comprises a proximal end 110, a tapered region 120, and a distal end 130. The proximal end 110 is the portion of the guide tip introducer 100 that mounts on to the anvil tip 210 of an existing endoscopic stapler 200. The tapered region 120 is the portion of the guide tip introducer 100 that transitions the shape and size of the proximal end 110 to the shape and size of the distal end 130. The distal end 130 is the extended tubular portion of the guide tip introducer 100 that protrudes from the anvil tip 210 and facilitates the positioning of the endoscopic stapler 200.

Figure 2:
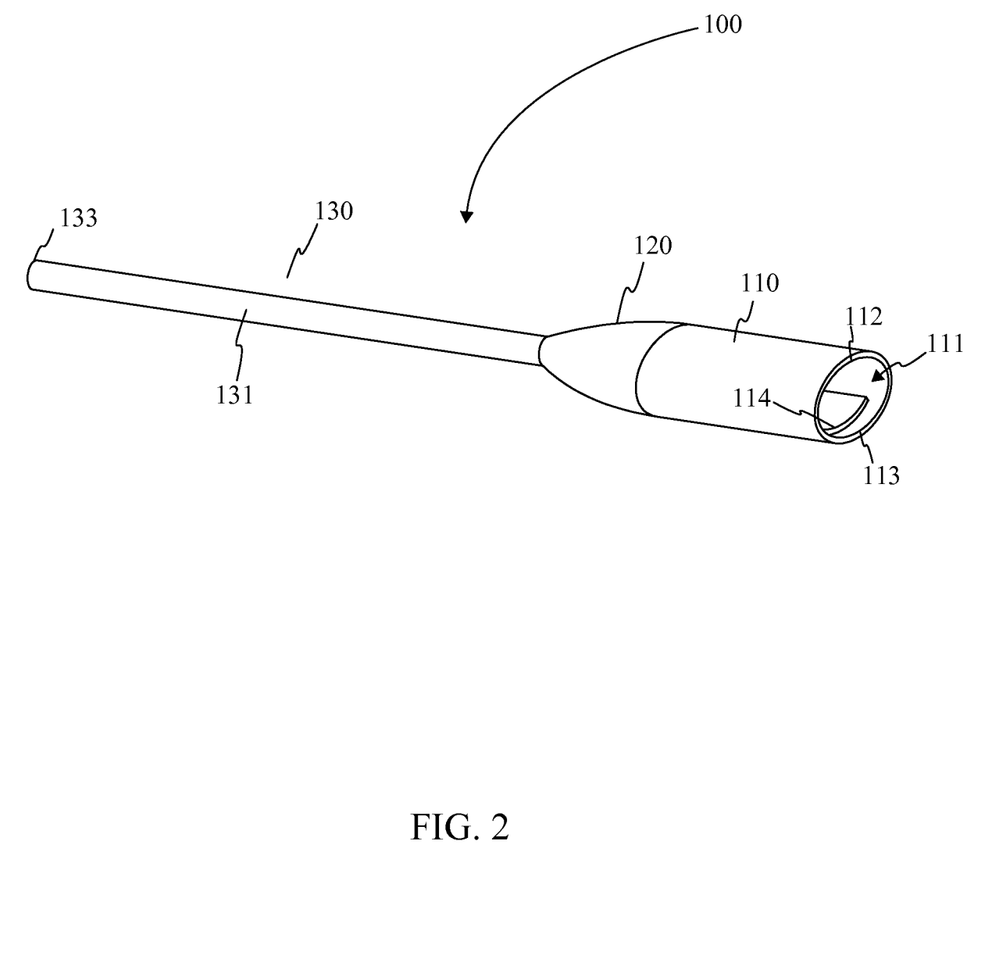
FIG. 2 is a rear perspective view displaying the guide tip introducer as per the current embodiment of the present invention.
Figure 3:
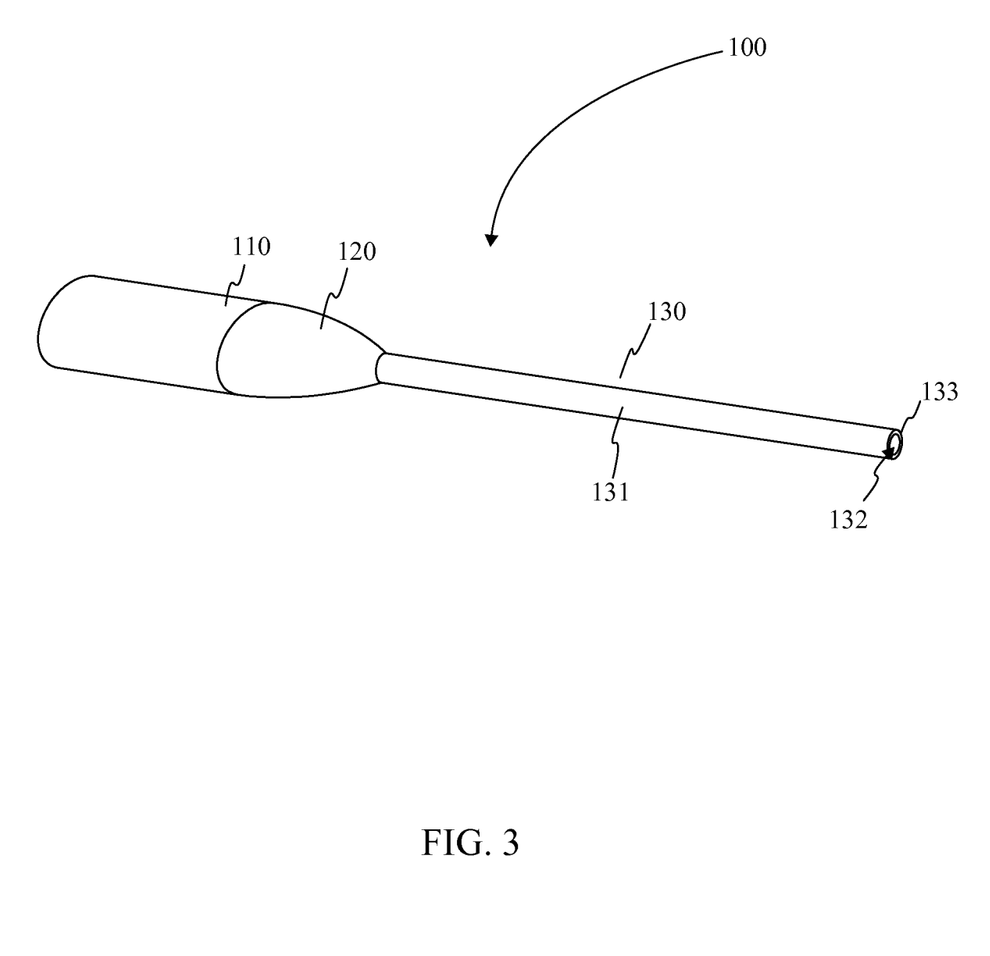
FIG. 3 is a front perspective view displaying the guide tip introducer as per the current embodiment of the present invention.
Figure 4:
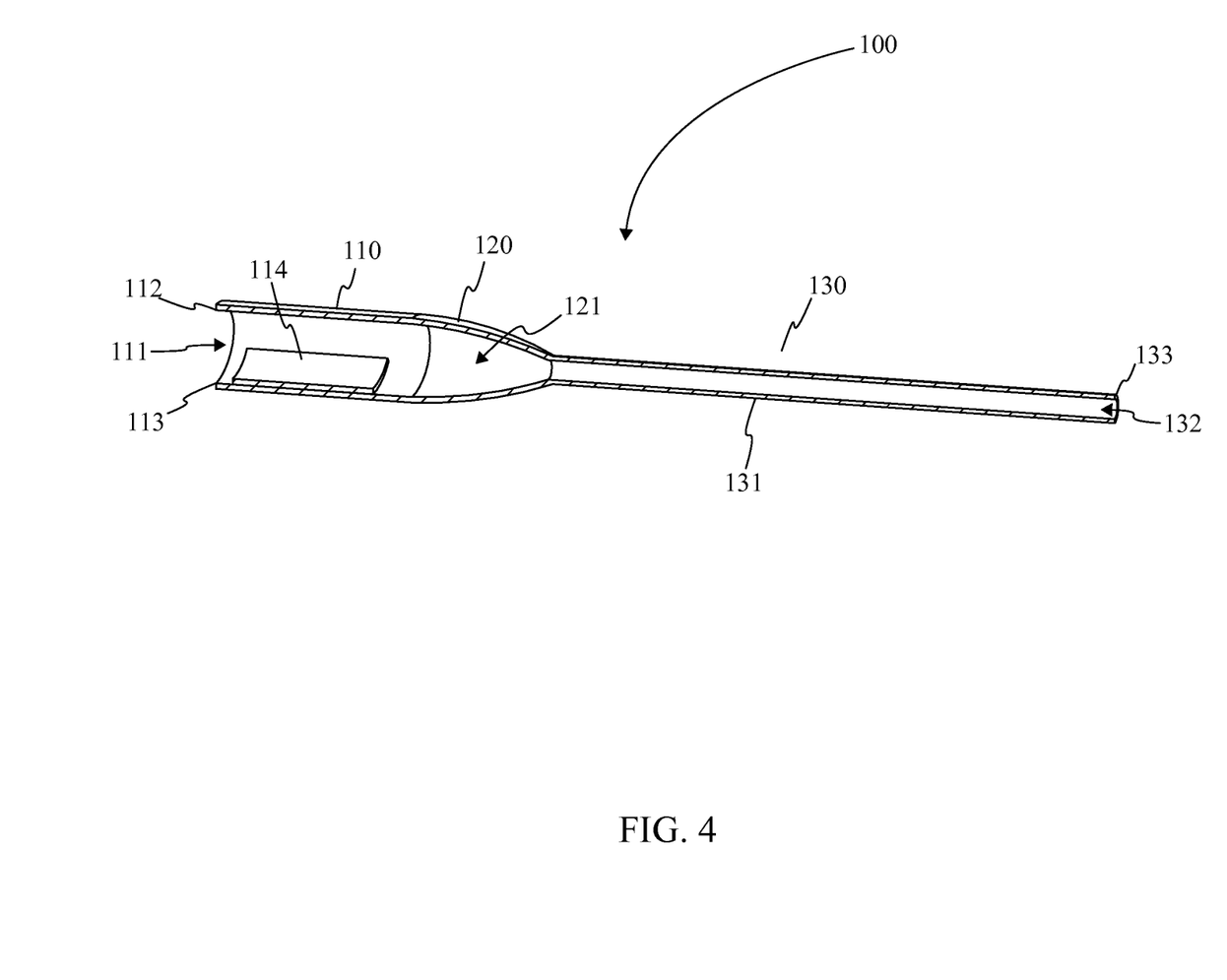
FIG. 4 is a cross sectional view displaying the interior component arrangement of the guide tip introducer as per the current embodiment of the present invention.

Referencing FIG. 2, FIG. 3, and FIG. 4, the guide tip introducer 100 mounts to the anvil tip 210 of the endoscopic stapler 200 through the proximal end 110. The proximal end 110 sleeves the anvil tip 210 and is magnetically secured to the metallic surface 212 to prevent detachment of the guide tip introducer 100 during a surgical procedure. The tapered region 120 is positioned between the proximal end 110 and the distal end 130. The tapered region 120 is positioned adjacent to the terminal end 213 of the anvil tip 210. The tapered region 120 transitions the shape of the proximal end 110 to the shape of the distal end 130.

Referencing FIG. 2, FIG. 3, and FIG. 4, the proximal end 110 is sleeved over the anvil tip 210 and magnetically secured to the magnetic surface. The proximal end 110 sleeves the stapling surface 211 and the metallic surface 212 of the anvil tip 210. In the current embodiment of the present invention, the proximal end 110 comprises an inner cavity 111. The inner cavity 111 is the space within the proximal end 110 that becomes coincident with the anvil tip 210. The inner cavity 111 is particularly formed to accept the anvil tip 210 with ease. The inner cavity 111 provides that the proximal end 110 is positioned around the anvil tip 210.

Referencing FIG. 2-4 and FIG. 7, the tapered region 120 is positioned between the proximal end 110 and the distal end 130. The tapered region 120 transitions the size and shape of the distal end 130 to the size and shape of the proximal end 110. The tapered region 120 transitions the wider shape of the proximal end 110 to the narrower and more elongated shape of the distal end 130. The tapered region 120 is found positioned adjacent to the terminal end 213 of the anvil tip 210. The tapered region 120 is particularly contoured to fit over the terminal end 213 of the anvil tip 210 while leaving a small gap. In the current embodiment of the present invention, the tapered region 120 comprises a headspace gap 121. The headspace gap 121 is a voided space within the tapered region 120 that is in fluid communication with the inner cavity 111. The headspace gap 121 works with the inner cavity 111 to accommodate the anvil tip 210. The headspace gap 121 contains the terminal end 213 of the anvil tip 210. The headspace gap 121 is found in fluid communication with the distal end 130. The fluid communication between the headspace gap 121 and the distal end 130 facilitates the removal of the guide tip introducer 100 from the anvil tip 210 by reducing negative pressure building up within headspace gap 121.

Referencing FIG. 2-7, the distal end 130 is the positioned opposite the proximal end 110 across the tapered region 120. In the current embodiment of the present invention, the distal end 130 comprises a flexible member 131. The flexible member 131 has an elongated tubular shape that protrudes from the tapered region 120. The flexible member 131 formed from a flexible material with a particular rigidity slightly greater than that of a blood vessel. The flexible member 131 is the portion of the guide tip introducer 100 that slides underneath a targeted structure in order to facilitate positioning of the endoscopic stapler 200.

Figure 7:
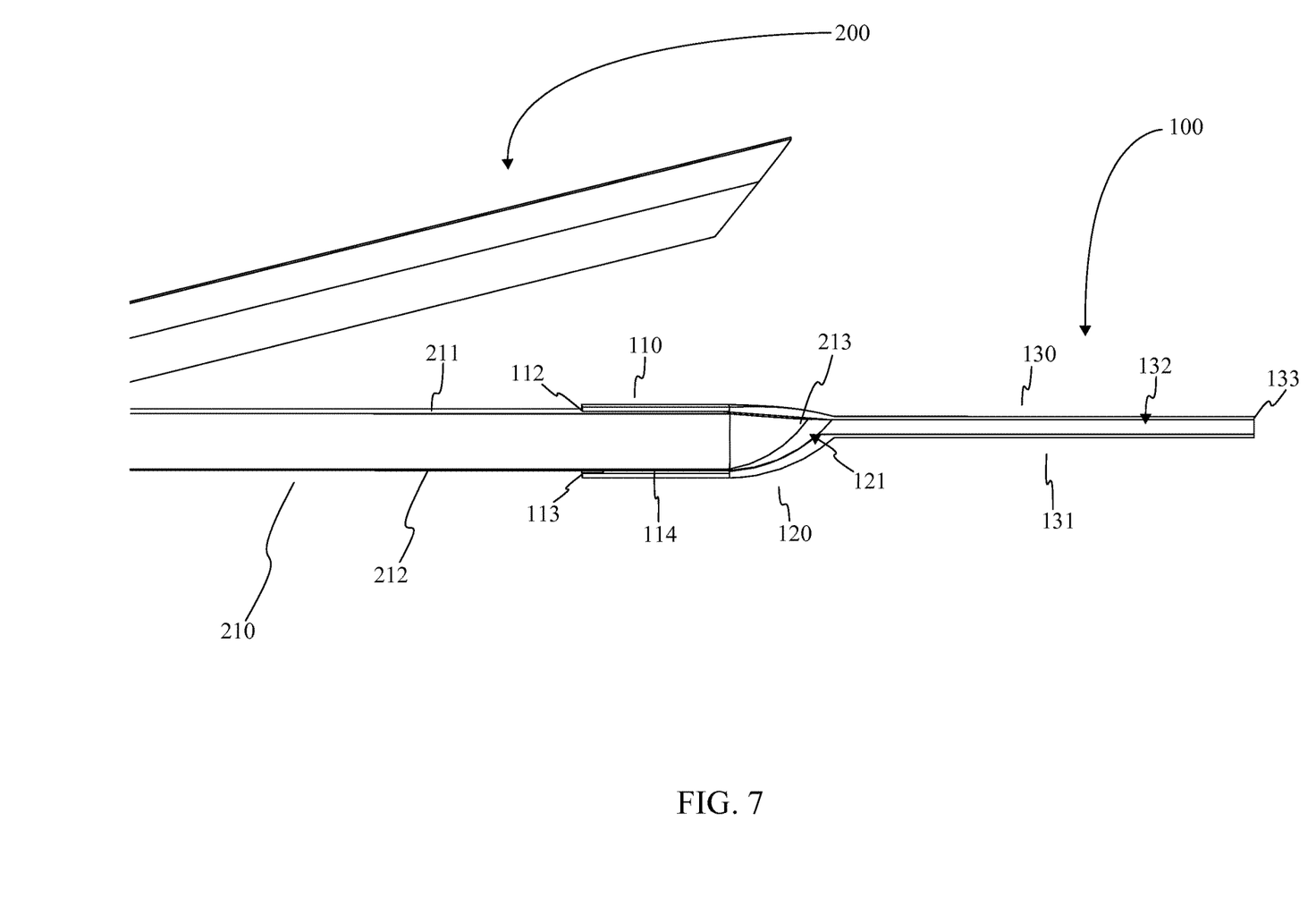
FIG. 7 is a cross sectional view displaying the guide tip introducer attached to the anvil tip as per the current embodiment of the present invention.

Referencing FIG. 4 and FIG. 7, the inner cavity 111 of the proximal end 110 engages the anvil tip 210 through various structural features that securely retain the guide tip introducer 100 to the endoscopic stapler 200. In the current embodiment of the present invention, the inner cavity 111 comprises a first surface 112, a second surface 113, and a magnetic strip 114. The first surface 112 and the second surface 113 are oppositely facing surface structures positioned across the inner cavity 111. The first surface 112 coincidently engages the stapling surface 211 of the anvil tip 210. The second surface 113 is positioned opposite the first surface 112 across the inner cavity 111. The second surface 113 is positioned adjacent to the metallic surface 212 of the anvil tip 210. The magnetic strip 114 is positioned between the second surface 113 and the metallic surface 212. The magnetic strip 114 is the provided as the engagement means for magnetically securing the proximal end 110 to the anvil tip 210. The magnetic strip 114 is adhered to the second surface 113 preventing detachment. The particular shape of the magnetic strip 114 changes the contours of the inner cavity 111 facilitating attachment to the anvil tip 210.

Referencing FIG. 2-7, the flexible member 131 is the long tubular structure of the distal end 130 that slides underneath a targeted structure. In the current embodiment of the present invention, the flexible member 131 comprises a lumen 132 and a flattened tip 133. The lumen 132 traverses through the entire length of the flexible member 131. The lumen 132 provides a particular rigidity to the flexible member 131 as the lumen 132 is a hollow structure positioned centrally throughout the flexible member 131. The flattened tip 133 is terminally positioned on the flexible member 131 opposite the positioning of the tapered region 120. The flattened tip 133 is particularly formed to slide past tissue without damaging it. The flattened tip 133 is traversed by the lumen 132. The lumen 132 is provides a means of preventing negative pressure from forming within the headspace gap 121. The lumen 132 accomplishes that by being in fluid communication with the headspace gap 121. By traversing through the flattened tip 133, negative pressure is equalized by air passing through the flattened tip 133.

The present invention comprises a method of creating the guide tip introducer 100. The guide tip introducer 100 is created using materials available in most standard operating rooms. The materials needed to create the guide tip introducer 100 comprise a red rubber catheter and a piece of magnetic tape. The red rubber catheter is a standard catheter principally comprising a drainage end, a tapered section, an elongated catheter body, and a drainage lumen. The piece of magnetic tape is cut from standard magnetic tapes found in a needle counting box.

Figure 5:
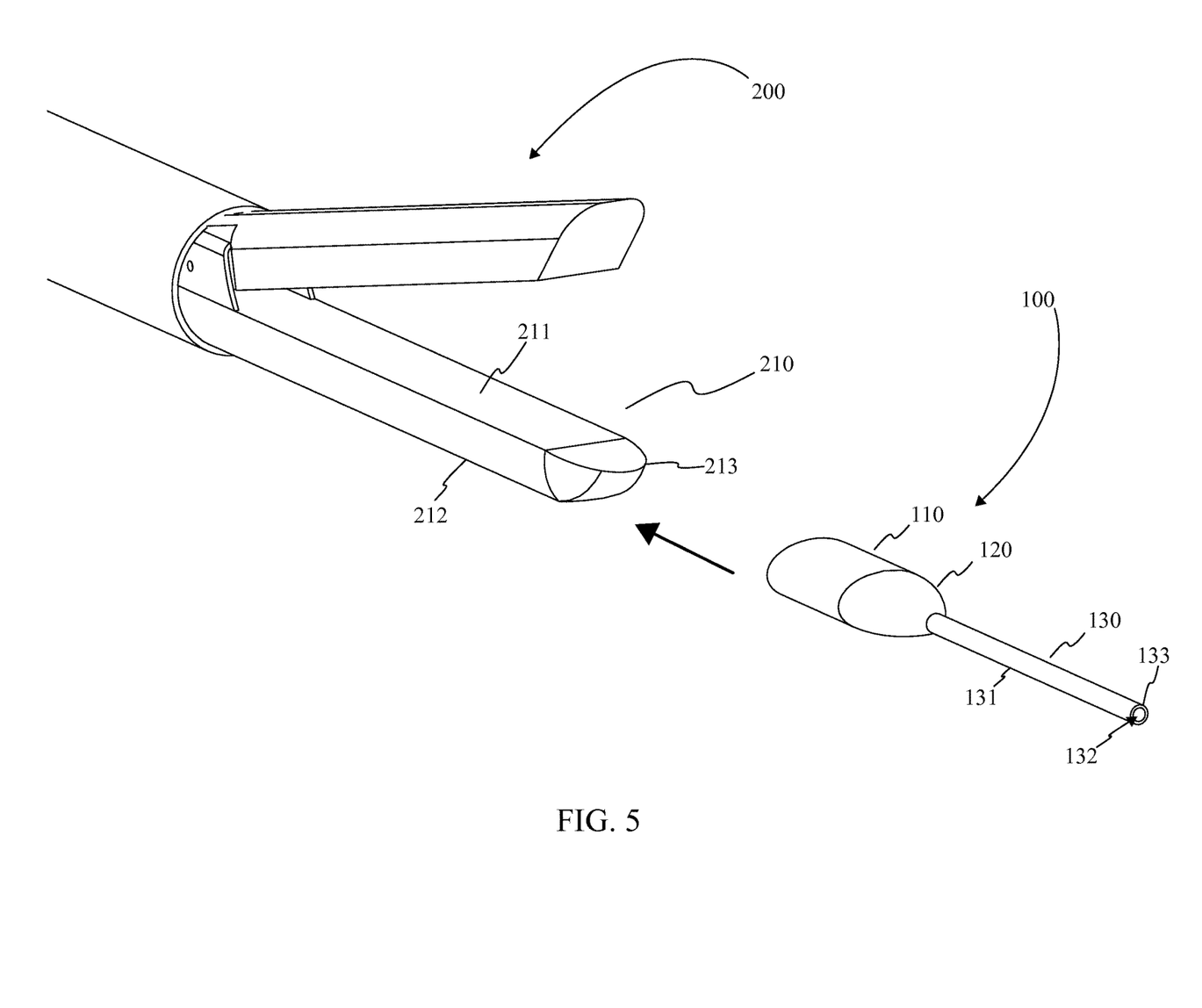
FIG. 5 is a perspective view displaying the mounting alignment of the guide tip introducer to the anvil tip of the endoscopic stapler as per the current embodiment of the present invention.
Figure 8:
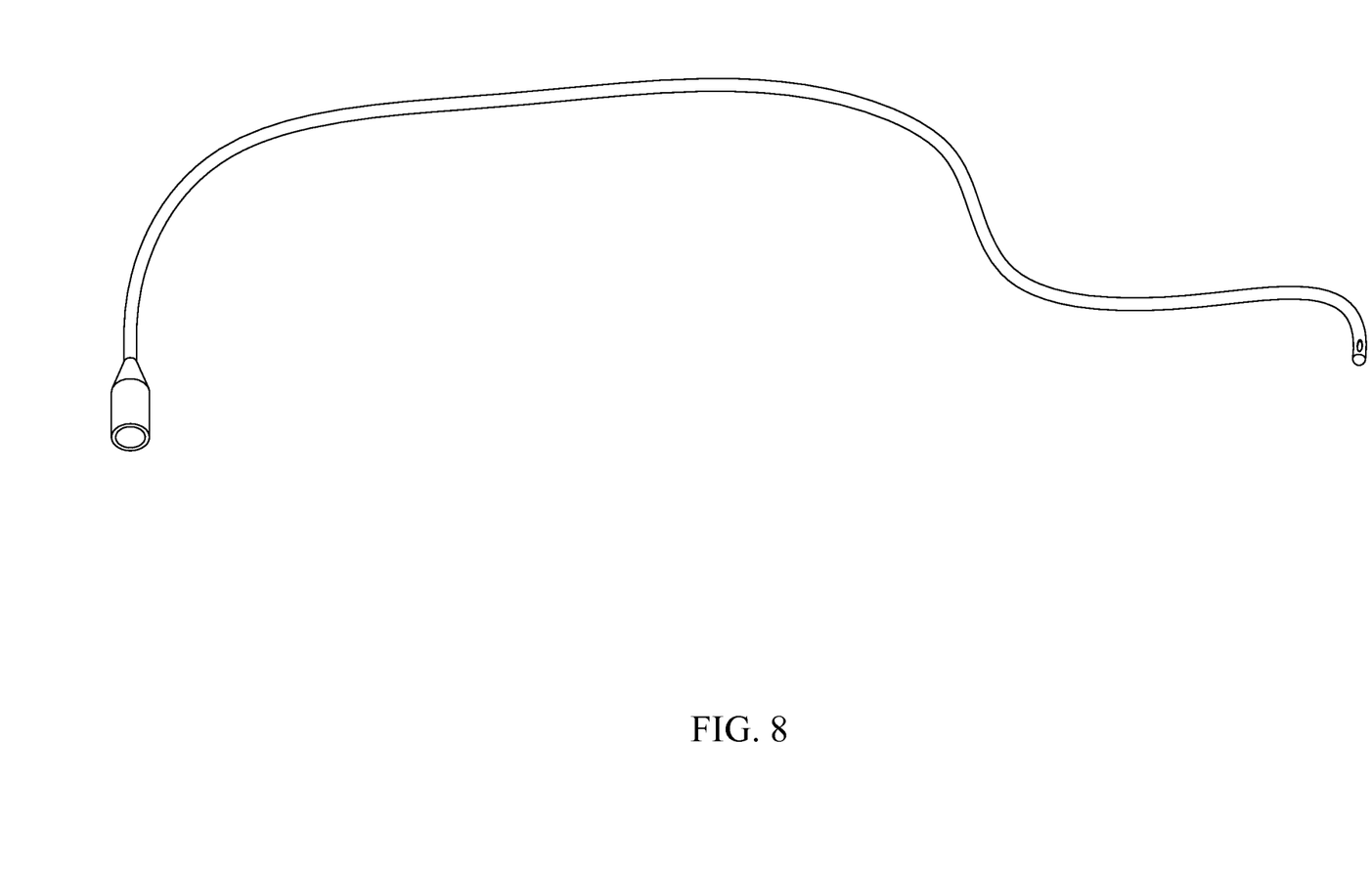
FIG. 8 is a perspective view displaying a red rubber catheter to be used in the creation of the guide tip introducer.

Referencing FIG. 2, FIG. 5, and FIG. 8, the red rubber catheter is sized to ensure proper fitment on the anvil tip 210 of the endoscopic stapler 200. The red rubber catheter is sized by comparing the opening of the drainage end to width of the anvil tip 210. The drainage end is sized to allow easy fitment over the anvil tip 210. Preferably, the drainage end is only slightly smaller in width than the anvil tip 210. The particular sizing of the drainage end provides a secure but easily removable fitment of the proximal end 110 of the guide tip introducer 100.

Figure 9:
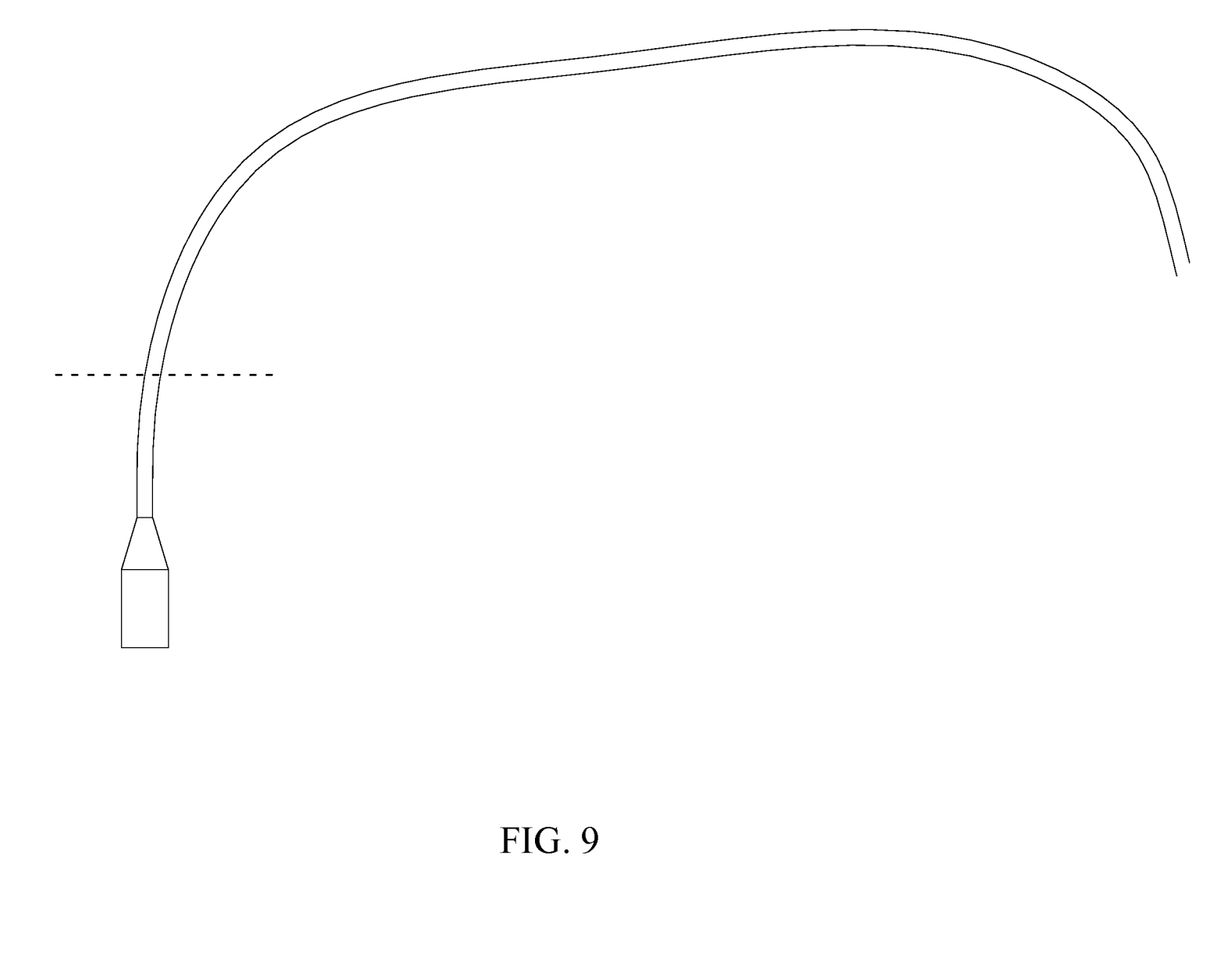
FIG. 9 is a top down view displaying a red rubber catheter with a cut line positioned through the elongated catheter body.
Figure 10:
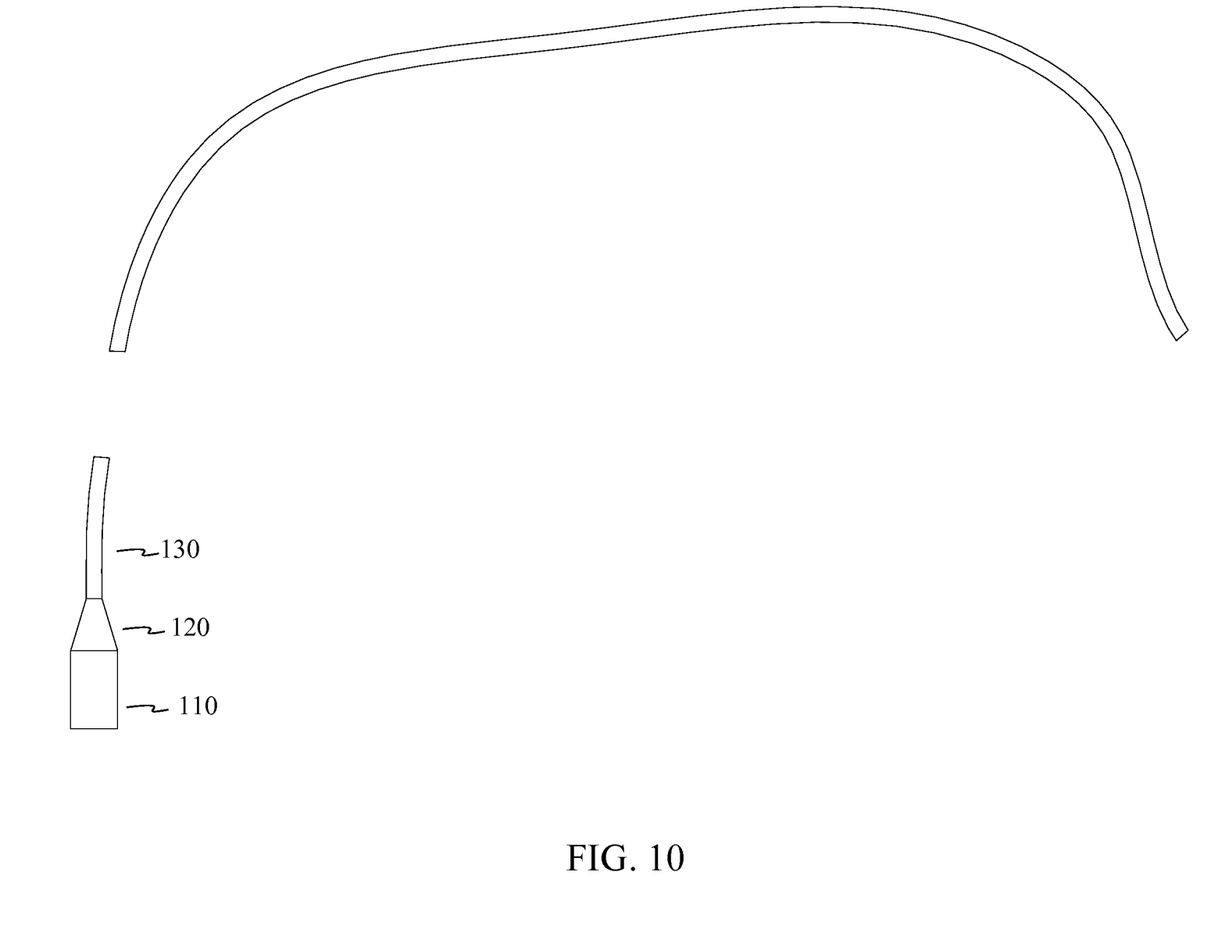
FIG. 10 a top down view displaying the red rubber catheter cut through the elongated catheter body.

Referencing FIG. 8, FIG. 9, and FIG. 10, the red rubber catheter is cut to a particular length after being appropriately sized. The elongated catheter body is cut proximal to the tapered section. The length of the elongated catheter body from the tapered section to the terminal end 213 forms the flexible member 131 of the guide tip introducer 100. The determination of the length of the flexible member 131 is done by the user and may vary depending on the particular requirement of the surgical procedure. Cutting the elongated catheter body exposes the drainage lumen that traverses through the red rubber catheter. The drainage lumen is analogous to the lumen 132 and provides a means of equalizing the pressure within the area corresponding to the headspace gap 121.

Referencing FIG. 2, FIG. 4, and FIG. 10, the piece of magnetic tape is sized for fitment within the drainage end. The piece of magnetic tape is cut from a larger strip of magnetic tape. The piece of magnetic tape is sized in order to fit on with the interior portion of the drainage end. The piece of magnetic tape is slightly larger than the width of the drainage end in order to provide particular contours to the drainage end when subsequently mounted. The particular contours facilitate the attachment of the drainage end to the anvil tip 210.

Referencing FIG. 2, FIG. 4, and FIG. 10, the piece of magnetic tape is mounted to the interior wall of the drainage end. The piece of magnetic tape that was sized to adequately fit the drainage end is mounted to an interior wall of the drainage end through the adhesive side of the magnetic tape. The adhesive side securely mounts the piece of magnetic tape to the interior wall. When mounted to the drainage end, the particular size and shape of the piece of magnetic tape alters the contours of the drainage end, forming an elliptical profile. The elliptical profile facilitates the mounting of the drainage end to the anvil tip 210.

Figure 6:
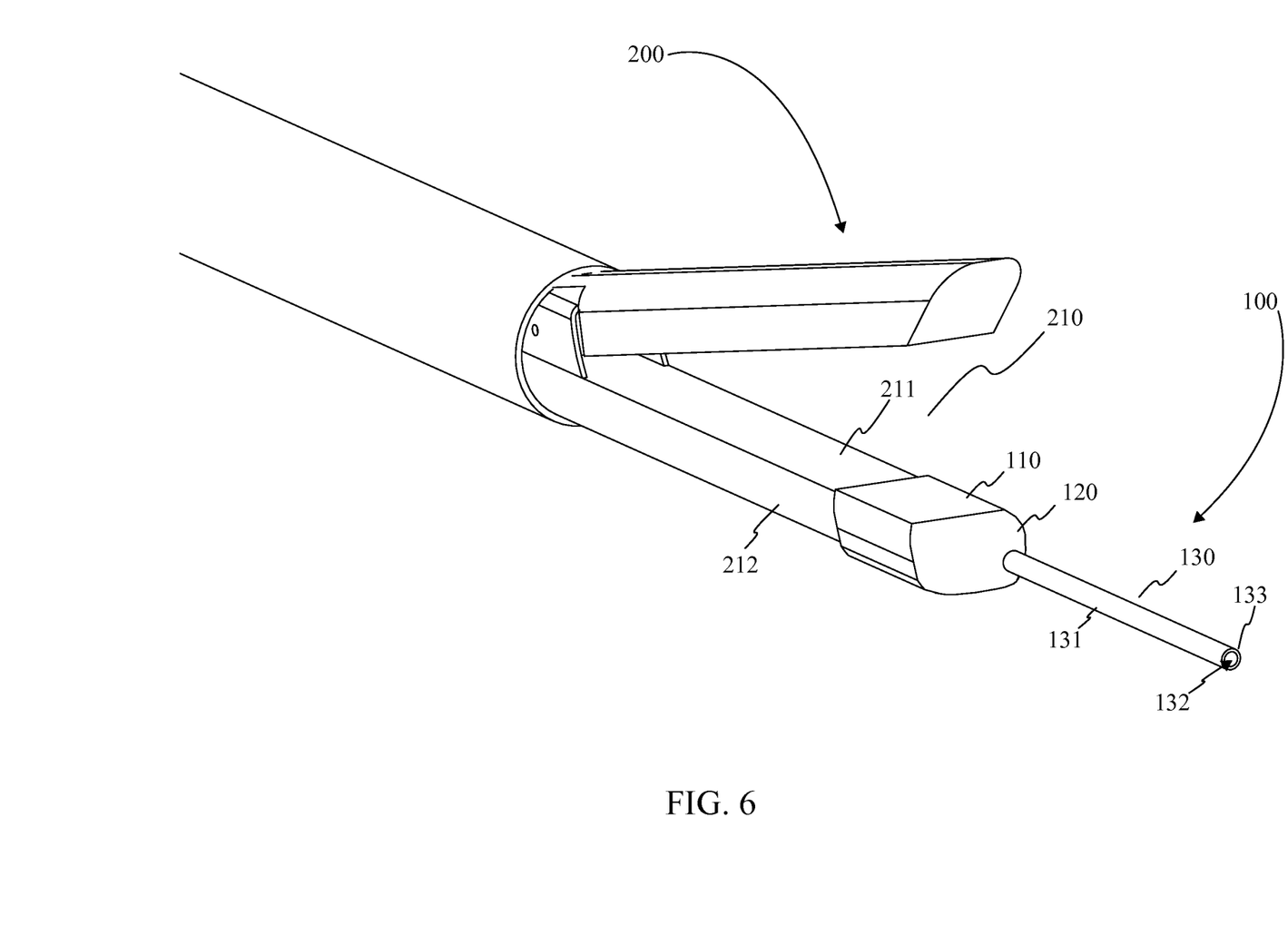
FIG. 6 is a perspective view displaying the guide tip introducer attached to the anvil tip as per the current embodiment of the present invention.

Referencing FIG. 5-6 and FIG. 10, the drainage end is attached to the anvil tip 210. The drainage end sleeves over the anvil tip 210. The piece of magnetic tape mounted to the interior wall of the drainage end aligns with the metallic surface 212 of the anvil tip 210. When the drainage end is made coincident with the anvil tip 210, the piece of magnetic tape magnetically engages the metallic surface 212 of the anvil tip 210. The magnetic engagement between the piece of magnetic tape and the metallic surface 212 retains securely retains the drainage end to the anvil tip 210 during a surgical procedure.

Figure 1:
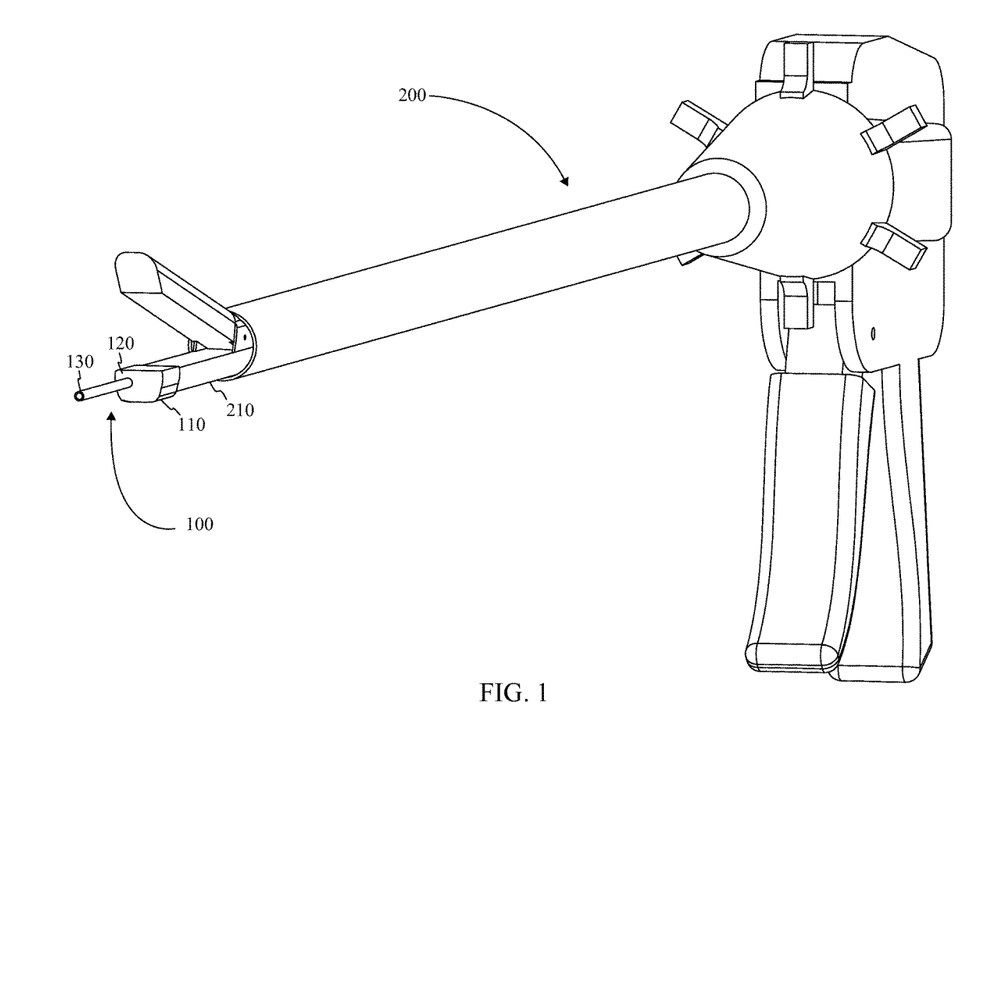
FIG. 1 is a perspective view displaying the guide tip introducer attached to an endoscopic stapler.

Referencing FIG. 1, the guide tip introducer 100 may be mounted to the anvil of a plurality of endoscopic staplers 200. The guide tip introducer 100 may function with Ethicon endoscopic staplers 200 and Covidean endoscopic staplers 200s, as well as any brand or model of endoscopic stapler 200 with an anvil tip 210 that would benefit from the use of a guide tip introducer 100.

The invention is a guide tip introducer for endoscopic stapler which is specifically designed to make it easier to maneuver the endoscopic stapler around arteries and veins, and underneath structures. This is particularly necessary in minimally invasive surgery where often the only way the surgeon operating the stapler can see into the body cavity is by way of two-dimensional images. The invention is intended to be compatible with a very broad range of makes and models of endoscopic staplers which are used by surgeons throughout the world. There are in existence some guide tips which serve a similar purpose to the invention, however these devices are specific to the respective make and model of endoscopic stapler for which they were designed. Thus, they are useless to surgeons who use a different make or model of endoscopic stapler. The invention is indeed to correct this oversight by introducing a guide tip with great interchangeability between different types of endoscopic stapler. The invention comprises a proximal end, a tapered region, a distal end, a central cavity, and a magnetic strip.

The proximal end is generally cylindrical, however it is comprise of a semi-flexible material such that it may deform into an oval or ellipsoidal shape. The proximal end is located at the rear of the invention, and is the component which, in conjunction with the central cavity, allows the invention to be slipped over the end of the anvil of the endoscopic stapler. The proximal end allows the invention to be mounted onto the end of the anvil. The diameter of the proximal end is appropriately the largest diameter of all the three sections of the invention; this is necessary in order to accommodate the width of the anvil. The length of the proximal end may vary depending upon how much of the invention is desired to slide over the anvil. More length in contact with the anvil means a better fit between them, however it also means more bulk for the invention. A balance must be struck between the bulk of the proximal end and the snugness of fit between the proximal end and the anvil of the endoscopic stapler.

The tapered region of the invention is generally conical in shape, and serves as a junction between the proximal end and the distal end. The difference in diameter between the proximal end and the distal end is rather large; this is primarily due to the fact that the proximal end must slide over the anvil while the distal end must help guide the anvil to its intended destination within the body cavity that is being operated in. The tapered region is a smooth loft between the proximal end and the tapered region, and ensures that the juncture between these two varying diameters is not sharp or rough. By ensuring a smooth connection between the proximal end and the distal end, the invention is very smooth and streamlined, and is far less likely to cause any damage to organic structures such as veins or arteries when it is being maneuvered around in the body cavity. The tapered region is fully integrated with both the proximal end and the distal end, and comprises the same material composition as the proximal end and the distal end.

The distal end is connected directly to the tapered region. The most prominent features of the distal end is the fact that the distal end protrudes outwards a significant distance from the tapered region. The distal end is what allows the invention to serve as a guide for the anvil. Any surgeon using an endoscopic stapler with the invention attached can use the distal end essentially as a sort of guide probe to line up the anvil with intended maneuvers. In this fashion, any movements made with the endoscopic stapler can be more precise and more deliberate, thereby drastically decreasing the chances of accidentally damaging some organic structure such as a vein or artery. The diameter of the distal end is significantly smaller than that of the proximal end. This is necessary to allow the distal end to be maneuvered in between and under certain structures. In addition to the small size and the length of the distal end contributing to its guide function, the distal end is also moderately flexible. This is necessary such that the distal end may potentially come into contact with the walls of the body cavity or other structures and harmlessly deflect off without puncturing or tearing any tissues. Additionally, the flexibility can add to the guiding potential of the invention as the surgeon could potentially initial a new maneuver at an angle and then use the follow the bend of the guide tip as the endoscopic stapler is angled into place. The exact material composition of the three sections of the invention may vary in the final embodiment of the invention, however it is important that the material chosen be at least somewhat flexible such that the distal end can flex and bend.

The central cavity of the invention is a hole which runs the entire length of the invention. The diameter varies throughout the invention; varying in conjunction with the changing diameters of the first, second, and distal ends. The diameter of the central cavity changes such that the invention has a uniform wall thickness throughout its structure. The primary purpose of the central cavity is twofold. The first and most important function of the primary cavity is to allow the invention to be slid onto the end of the anvil. By providing a significant gap in the proximal end, the anvil can be slid into this gap, thereby placing the invention in firm contact with the anvil. The second, and related, function of the central cavity is to ensure that the invention is easy to slide onto and easy to slide off of the anvil. In some cases the size of the anvil may be such that the proximal end fits snugly around the anvil. In such cases it would be possible for air to be trapped within the proximal end and the tapered region. Sliding the anvil in further would compress the trapped air, making it difficult to slide the invention all the way into place. By providing that the central cavity traverses entirely through the invention, no air can be trapped, as any air within the proximal end and tapered region is simply pushed out of the invention through the distal end which is traversed by the central cavity. This same concept also makes it very easy to remove the invention, which may be necessary during surgery, as pressure is kept equalized within and without the invention thanks to the central cavity.

The final component of the invention is the magnetic strip. The magnetic strip is a very important component of the invention. The magnetic strip is placed within the central cavity in the proximal end. The primary purpose of the magnetic strip is to ensure that the invention stays securely on the anvil when the endoscopic stapler is in use. Most anvils on endoscopic staplers are metallic, thereby allowing the magnetic strip to secure the invention to the anvil through magnetic attraction. The magnetic strip itself may be either chemically adhered to, or physically embedded within the proximal end. The magnetic strip also serves to flatten the proximal end and help it take on the shape of the anvil to which the invention is attached. This further streamlines the invention and ensures that it is less likely to catch on external structures. The magnetic strip may also allow the invention to be attached to the anvil even if the anvil is smaller than the proximal end, as the magnetic attraction between the anvil and the magnetic strip holds the invention in place. The exact length, width, and thickness of the magnetic strip may vary in the final embodiment of the invention, however it is important that the length of the magnetic strip does not exceed the length of the proximal end by an excessive amount. Likewise it is important that the width and thickness of the magnetic strip be kept minimal such that the magnetic strip does not obstruct the invention from sliding onto the anvil of the endoscopic stapler.

Although the invention has been explained in relation to its preferred embodiment, it is to be understood that many other possible modifications and variations can be made without departing from the spirit and scope of the invention as hereinafter claimed.

What is claimed is:

1. A guide tip introducer for mounting onto existing endoscopic staplers comprising:
    a proximal end;
    a tapered region;
    a distal end;
    a magnetic strip;
    the proximal end comprising an inner cavity;
    the tapered region comprising a headspace gap;
    the distal end comprising a flexible member;
    the inner cavity comprising a first surface and a second surface;
    the flexible member comprising a lumen and a flattened tip;
    the tapered region being positioned between the proximal end and the distal end;
    the tapered region being tapered from the proximal end towards the distal end;
    the magnetic strip being securely mounted to the second surface;
    the inner cavity being conformed to the magnetic strip by the magnetic strip serving to flatten the proximal end.

2. The guide tip introducer for mounting onto existing endoscopic staplers as claimed in claim 1 comprising:
    the inner cavity being positioned in fluid communication with the headspace gap;
    the lumen traversing through the flexible member; and
    the lumen being in fluid communication with the headspace gap.

3. The guide tip introducer for mounting onto existing endoscopic staplers as claimed in claim 1 comprising:
    the first surface being positioned opposite the second surface across the inner cavity.

4. The guide tip introducer for mounting onto existing endoscopic staplers as claimed in claim 1 comprising;
    the flattened tip being traversed by the lumen; and
    the flattened tip being terminally positioned on the flexible member opposite the tapered region.

5. A guide tip introducer for mounting onto existing endoscopic staplers comprising:
    a proximal end
    a tapered region;
    a distal end;

a magnetic strip;
the proximal end comprising an inner cavity;
the tapered region comprising a headspace gap;
the distal end comprising a flexible member;
the inner cavity comprising a first surface and a second surface;
the flexible member comprising a lumen and a flattened tip;
the tapered region being positioned between the proximal end and the distal end;
the tapered region being tapered from the proximal end towards the distal end;
the inner cavity being positioned in fluid communication with the headspace gap;
the lumen traversing through the flexible member;
the lumen being in fluid communication with the headspace gap;
the first surface being positioned opposite the second surface across the inner cavity;
the magnetic strip being securely mounted to the second surface;
the inner cavity being conformed to the magnetic strip by the magnetic strip serving to flatten the proximal end;
the flattened tip being traversed by the lumen; and
the flattened tip being terminally positioned on the flexible member opposite the tapered region.

6. A method of creating a guide tip introducer as claimed in claim 1 for an existing endoscopic stapler using a urinary catheter comprising the steps of:
providing a red rubber catheter comprising a drainage end, a tapered section, an elongated catheter body, and a drainage lumen;
providing a piece of magnetic tape;
sizing the red rubber catheter to ensure fitment on the anvil tip of an endoscopic stapler, wherein the drainage end should easily fit over the anvil tip of the endoscopic stapler;
cutting the elongated catheter body proximal to the tapered section, wherein the elongated catheter body is shorted to a preferred length from the tapered section and exposes the drainage lumen;
sizing the piece of magnetic tape for fitment within the drainage end of the red rubber catheter;
mounting the sized piece of magnetic to an interior wall of the drainage end, wherein the mounted piece of the magnetic tape alters the shape of the drainage end; and
attaching the drainage end with the mounted piece of magnetic tape to the anvil of an endoscopic stapler, wherein the mounted piece of magnetic tape magnetically secures the drainage end to the metallic surface of the anvil tip of the endoscopic stapler.

* * * * *